United States Patent
Fischell et al.

(10) Patent No.: US 6,270,521 B1
(45) Date of Patent: Aug. 7, 2001

(54) STENT DELIVERY CATHETER SYSTEM FOR PRIMARY STENTING

(75) Inventors: Robert E. Fischell, Dayton, MD (US); David R. Fischell, Fair Haven, NJ (US); Mark L. Pomeranz, Weston; Nicholas A. Green, Hollywood, both of FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/316,843

(22) Filed: May 21, 1999

(51) Int. Cl.[7] .................................................. A61F 11/00
(52) U.S. Cl. ............................................................. 623/1.11
(58) Field of Search ................................. 606/108, 192, 606/193, 194, 195, 198; 623/1.11

(56) References Cited

U.S. PATENT DOCUMENTS

| | | | |
|---|---|---|---|
| 4,739,762 | * 4/1988 | Palmaz | 623/1.11 |
| 4,768,507 | 9/1988 | Fischell et al. . | |
| 5,376,376 | * 12/1994 | Li | 606/108 |
| 5,639,274 | 6/1997 | Fischell et al. . | |
| 5,653,689 | * 8/1997 | Bueina et al. | 606/108 |
| 5,735,859 | 4/1998 | Fischell et al. . | |
| 5,743,874 | 4/1998 | Fischell et al. . | |
| 5,782,855 | * 7/1998 | Lau et al. | 606/108 |
| 5,792,144 | * 8/1998 | Fischell et al. | 606/108 |

* cited by examiner

Primary Examiner—Gene Mancene
Assistant Examiner—Eduardo C. Robert
(74) Attorney, Agent, or Firm—Paul A. Coletti

(57) ABSTRACT

An ultra-thin distal sheath section of the sheathed system uses heat shrinkable elastomer tubing with a wall thickness that is less than 0.05 mm and may be less than 0.025 mm. There are two methods for securing the ultra-thin distal sheath section over the distal tip. A first method is to employ another thin tube shrunk down over the distal end of the ultra-thin distal sheath. It is also envisioned that simply shrinking the ultra-thin distal sheath section down on the tapered section of the distal tip will hold it securely. A monorail (rapid exchange) version of this stent delivery system is also envisioned. A second version uses radioopaque elastic bands mounted over the ends of the balloon just proximal and just distal to the stent to provide a low profile for a primary stent delivery system. These radioopaque elastic bands could contain a high-density material such as tungsten to make them radioopaque and eliminate the need for radioopaque markers normally attached to the angioplasty balloon inner shaft.

39 Claims, 7 Drawing Sheets

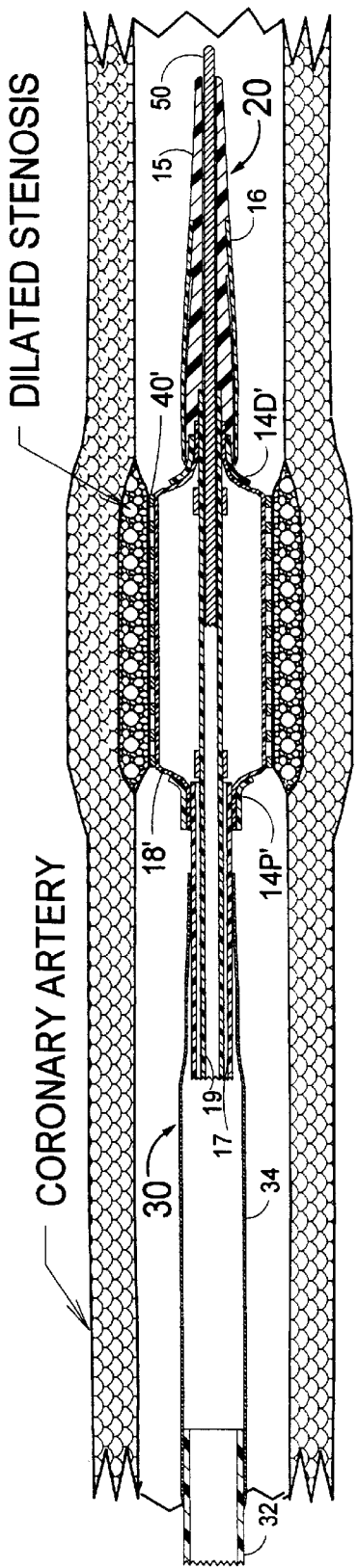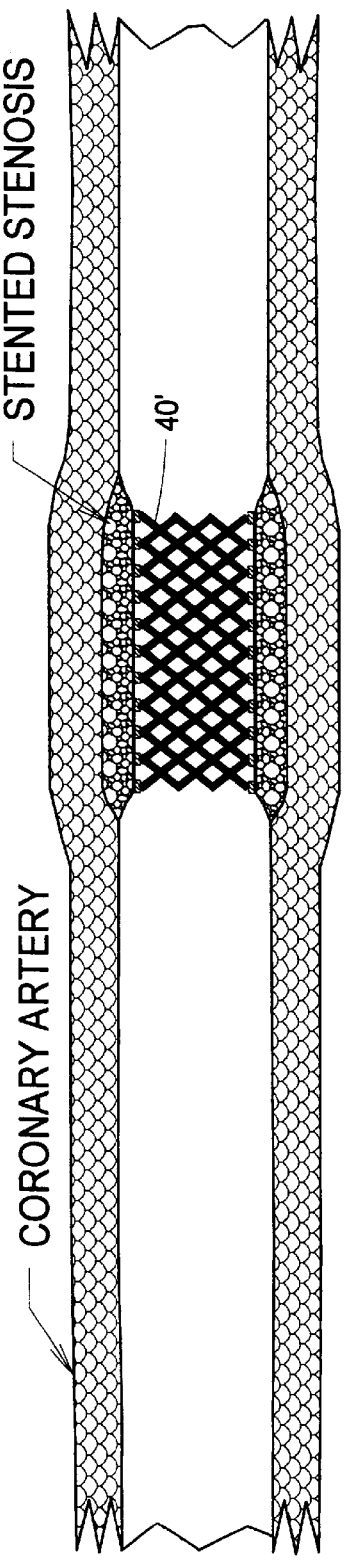

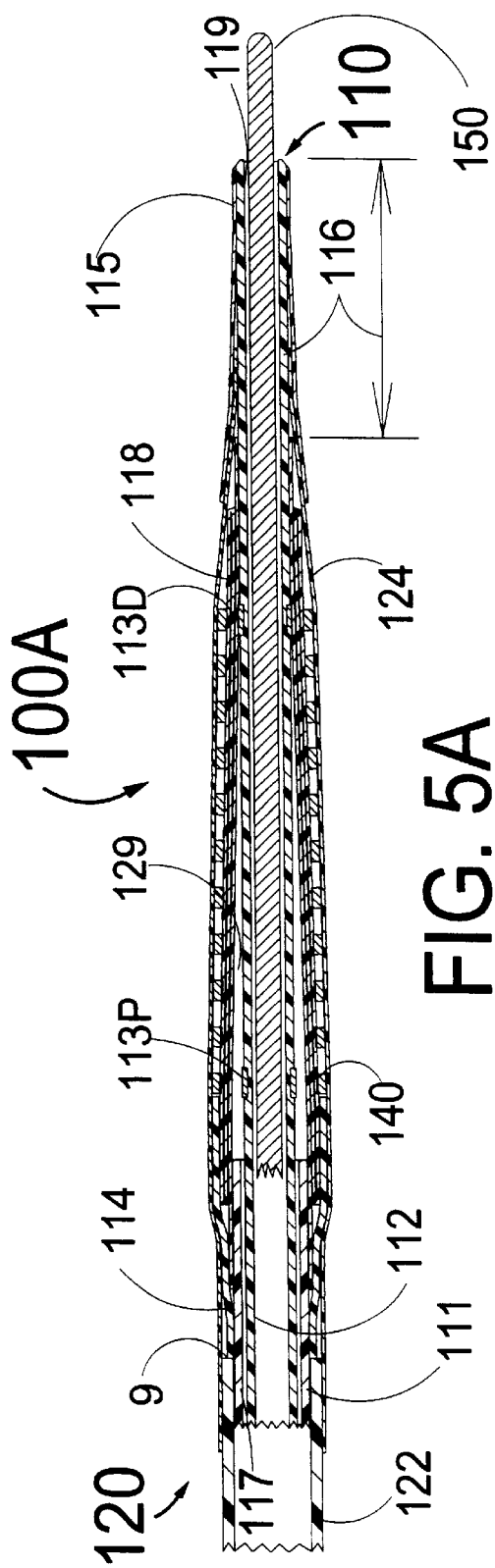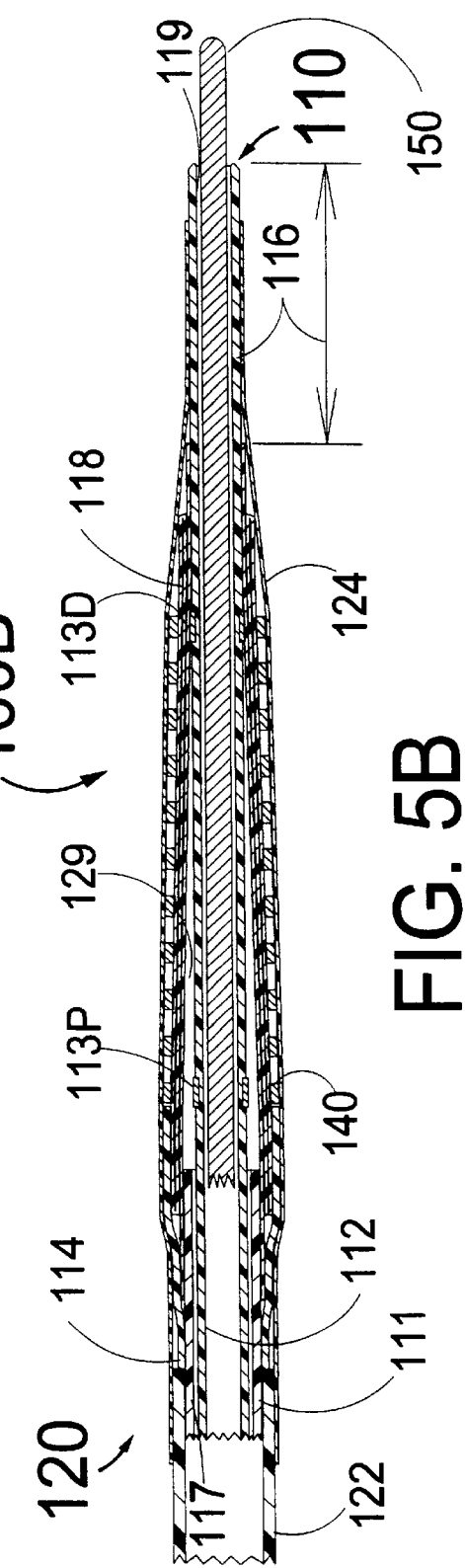
FIG. 5A
FIG. 5B

STENT DELIVERY CATHETER SYSTEM FOR PRIMARY STENTING

FIELD OF USE

This invention is in the field of catheters to place stents into a stenosis in a vessel of a human body.

BACKGROUND OF THE INVENTION

Intravascular stents are well known in the field of interventional cardiology for the treatment of arterial stenoses. When placed through the body's vascular system, most stents are mounted onto a balloon angioplasty catheter with or without a cylindrical sheath that covers the stent prior to stent deployment by balloon expansion at the site of a dilated stenosis. If a sheath is not used, the stent can get caught on a calcified plaque or on the guiding catheter during movement into or out of the patient's body. This can cause the stent to come off the delivery catheter and embolize into the vasculature. When a sheath is used, it can have a few disadvantages. A first disadvantage is that most prior art sheaths are secured only at the stent delivery catheter's proximal end. Therefore, in order to have sufficient column strength, the sheath must be relatively thick-walled, making it stiff and bulky so that passage through tortuous coronary arteries can be difficult. Another disadvantage of prior art sheaths is that they have blunt distal ends that can catch on an already deployed stent, or on a calcified piece of intimal dissected tissue or on a tight stenosis. Still further, when secured only at the proximal end of a stent delivery catheter, the sheath often either uncovers the stent due to significant bending of the stent delivery catheter or the sheath advances too far distally beyond the distal end of the stent.

Because of the comparatively larger diameter, blunt end and stiffness of extant sheathed stent delivery systems or because of the rough outer surface of unsheathed stent delivery systems, pre-dilatation with another balloon angioplasty catheter is almost always required before stent implantation. It is highly desirable to be able to deliver a stent without pre-dilatation. The procedure of deploying a vascular stent without pre-dilatation and post-dilatation is called "primary stenting". In U.S. Pat. No. 5,792,144, Fischell et al describe a primary stenting system having a membrane sheath over the distal section of the catheter which holds the stent. While the Fischell device provides the capability for primary stenting, it may not hold the distal end of the membrane sheath with sufficient firmness to prevent it from uncovering the stent during passage through curved or calcified vessels. In addition, the membrane sheath of the Fischell et al invention adds several thousandths of an inch to the stent system profile. It would be advantageous if the stent delivery systems' outside diameter could be made smaller by shrinking the membrane sheath down onto the stent or, alternatively, having a primary stenting system without a membrane sheath.

SUMMARY OF THE PRESENT INVENTION

The present invention is a stent delivery catheter system for placing a stent within a stenosis in a vessel of a human body without the need for either pre-dilatation of the stenosis or post-dilatation of the stent. The primary stenting delivery catheter system utilizes the combination of low profile (i.e., a small outer diameter) with a continuous, smooth and lubricious outer surface extending backward from a tapered distal tip. This design makes it possible for the stent delivery catheter to be pushed through even very tight stenoses without requiring pre-dilatation.

Two versions of the primary stent delivery system are envisioned. The first version is a sheathed primary stenting system with a two-part sheath having a thick-walled proximal section and an ultra-thin distal section that is shrunk down to secure it to the catheter's distal tip. This embodiment differs from the prior art Fischell et al device that does not shrink its membrane sheath down over the stent and over the balloon catheter's distal tip.

For the first version which is a sheathed primary stenting system, the preferred embodiment of the ultra-thin distal sheath section of the sheathed system uses heat shrinkable elastomer tubing with a wall thickness that is less than 0.05 mm and may be less than 0.025 mm. There are two methods for securing the ultra-thin distal sheath section over the distal tip. A preferred method is to employ another thin tube shrunk down over the distal end of the ultra-thin distal sheath. It is also envisioned that simply shrinking the ultra-thin distal sheath section down on the tapered section of the distal tip will hold it securely. A monorail (rapid exchange) version of this stent delivery system is also envisioned.

The second version of the present invention is an unsheathed primary stenting system. The unsheathed primary stenting system uses radiopaque elastic bands mounted over the ends of the balloon just proximal and just distal to the stent to provide the lowest possible profile for a primary stent delivery system without the risk of stent embolization. These radiopaque elastic bands could contain a high-density material such as tungsten to make them radiopaque and eliminate the need for radiopaque markers normally attached to the angioplasty balloon inner shaft which markers can increase the device profile.

Thus, an object of this invention is to have a low profile primary stenting system that has a sheath with an ultra-thin distal section that is shrunk down over the stent and over the distal tip of the catheter.

Another object of this invention is to have a sheathed primary stenting system with an outer diameter, i.e., a profile of less than 1.1 mm.

Still another object of this invention is to have a primary stenting system with a sheath having a distal section with wall thickness of less than 0.05 mm.

Still another object of this invention is to have a primary stenting system with a sheath having a distal section with wall thickness of less than 0.025 mm.

Still another object of this invention is to have a primary stenting system with a sheath having a distal section that is made from a heat shrinkable or solvent swelled elastomer tubing.

Still another object of this invention is to have a primary stenting system with a sheath having a distal section that is made from a nylon material.

Still another object of this invention is to have a primary stenting system with a sheath that is lubricity coated.

Still another object of this invention is to utilize elastic tubes placed just proximal and just distal to the stent as a means to prevent stent embolization for an unsheathed primary stenting system.

Still another object of this invention is to have a stent delivery catheter system that utilizes a gently tapered, lubricious coated, highly flexible elastomer tip in order to have a distal section of the stent delivery catheter system that can be readily pushed through a tight stenosis.

Still another object of this invention is to have a primary stenting system that can place a stent into a tight stenosis without first pre-dilating that tight stenosis.

Still another object of this invention is to have a sheathed primary stenting system with rapid exchange capability.

These and other objects and advantages of this invention will become apparent to a person of ordinary skill in this art upon careful reading of the detailed description of this invention including the drawings as presented herein.

BRIEF DESCRIPTION OF THE DRAWINGS

FIG. 2D shows a longitudinal cross section of the distal section of the stent delivery catheter system with the balloon inflated and the stent deployed outward so as to dilate the stenosis.

FIG. 2E is a longitudinal cross section of the dilated stenosis showing the stent deployed radially outward and the stent delivery catheter system removed from the patient's artery.

FIG. 5A is a longitudinal cross section of the distal portion of an alternative embodiment of the sheathed primary stenting system.

FIG. 5B is a longitudinal cross section of a minor variation of the distal portion of the sheathed primary stenting system of FIG. 5A.

DETAILED DESCRIPTION OF THE DRAWINGS

Figure 1:
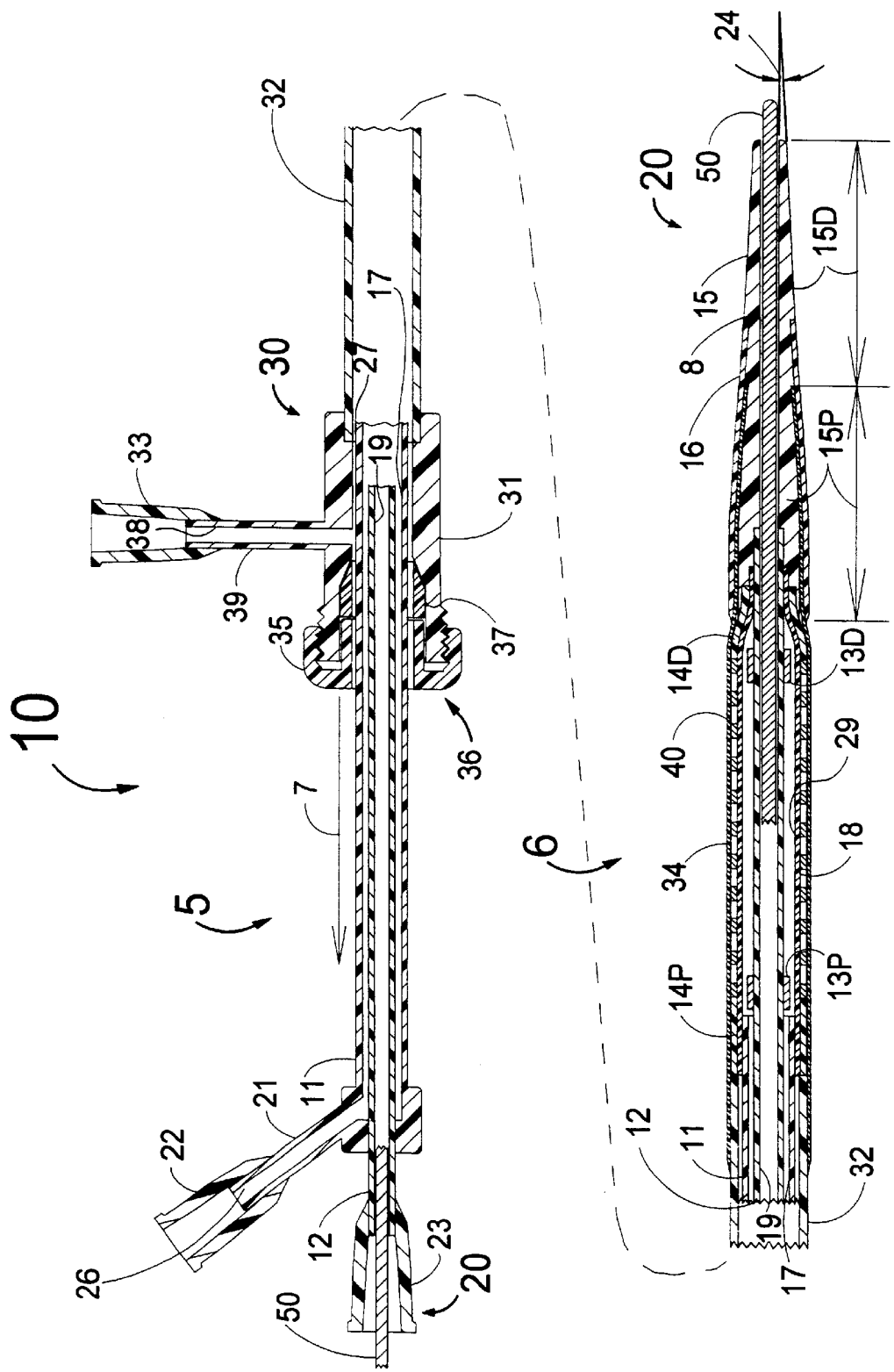
FIG. 1 is a longitudinal cross section of a sheathed primary stenting system that illustrates the structure of the proximal and distal sections of the primary stenting system.

FIG. 1 is a longitudinal cross section of a primary stenting system 10 shown in its pre-deployment configuration that is formed in two sections, namely; a proximal section 5 and a distal section 6. The primary stenting system 10 consists of a balloon angioplasty catheter 20, a slideable sheath 30, a stent 40 and a guide wire 50.

The balloon angioplasty catheter 20 consists of an outer shaft 11, an inner shaft 12, a proximal radiopaque marker band 13P, a distal radiopaque marker band 13D, a proximal elastomer band 14P, a distal elastomer band 14D, an inflatable angioplasty balloon 18 and a gradually tapered elastomer distal tip 15. The gradually tapered distal tip 15 has a gradually tapered proximal portion 15P and a gradually tapered distal portion 15D. The gradually tapered distal tip 15 has an average taper angle 24 that is typically less than 4 degrees and may be under 1 degree for devices designed for small diameter blood vessels. At the proximal end of the balloon angioplasty catheter 20 is a luer fitting 23 through which the guide wire 50 can be passed into the central lumen 19 of the inner shaft 12. Also at the proximal end of the balloon angioplasty catheter 20 is a side arm 21 having a luer fitting 22 and a central passageway 26. The central passageway 26 is in fluid communication with the annular passageway 17 that lies between the inner surface of the outer shaft 11 and the outer surface of the inner shaft 12. The balloon angioplasty catheter 20 also has at its distal section 6 an angioplasty balloon 18 whose interior chamber 29 is in fluid communication with the annular passageway 17 and the central lumen 26 of the side arm 21. Thus a source of inflation fluid can be inserted into or removed from the lumen 26 to inflate and deflate the balloon 18. Mounted on the balloon 18 is a balloon expandable stent 40 of any design that is well known in the art of balloon expandable stents.

The slideable sheath 30 is situated coaxially about the balloon angioplasty catheter 20. The sheath 30 has a Tuohy-Borst fitting 36 at the proximal end of the sheath 30, an ultra-thin distal section 34 and a sheath proximal section 32 having a proximal end attached to the Tuohy-Borst fitting 36 and a distal end attached to the ultra-thin distal section 34. The Tuohy-Borst fitting 36 has a main body 31 having a side arm 39 with a luer fitting 33. The side arm 39 has a central lumen 38 that is in fluid communication with the annular passageway 27 that lies between the interior surface of the sheath proximal section 32 and the exterior surface of the outer shaft 11. The main body 31 of the Tuohy-Borst fitting has a threaded proximal end onto which a nut 35 can be screwed on or off. Advancing the nut 35 compresses the elastomer gland 37 thus causing a fluid seal to be made against the outer surface of the outer shaft 11. When such a fluid seal exists, liquid can be injected through the lumen 38 of the side arm 39 to flush air out of the annular passageway 27.

The ultra-thin distal section 34 is shrunk down onto the proximal elastomer band 14P, the stent 40, the distal elastomer band 14D and the proximal portion 15P of the gradually tapered distal tip 15. A securing tube 16 fixedly attached at its distal end to the distal tip 15 is shrunk tight down over the distal portion of the ultra-thin distal section 34 thereby securing it during delivery of the primary stenting system 10 into the human body. Although the securing tube 16 holds the ultra-thin distal section 34 against the distal tip 15, the ultra-thin distal section 34 can still be pulled proximally out from under the securing tube 16 so as to unsheathe the stent 40. It should be noted that the distal tip 15 is molded so that there will be a continuous outer surface at the transition 8 from the distal tip 15 to the securing tube 16.

The sheath proximal section 32 has a distal end 9 that is in contact with the proximal end of the proximal elastomer band 14P. This causes the push force exerted at the proximal end of the sheath 30 to be transferred from the sheath proximal section 32 through the proximal elastomer band 14P, stent 40 and distal elastomer band 14D to the distal tip 15 thereby enhancing penetration through a tight stenosis. In addition to providing a transfer of push force, the elastomer bands 14P and 14D will prevent the stent 40 from sliding in either a proximal or distal direction and therefore reduce the probability of stent embolization. The elastomer bands 14P and 14D are typically made from a highly elastic material such as polyurethane or silicone rubber.

The sheath 30 is pulled back during stent deployment by first loosening the nut 35 of the Tuohy-Borst fitting 36, then sliding the Tuohy-Borst fitting 36 in a proximal direction (as shown by the arrow 7) while holding fixed the luer fitting 23 at the proximal end of the balloon angioplasty catheter 20. This will retract the ultra-thin distal section 34 from under the securing tube 16 and pull it back far enough beyond the proximal end of the angioplasty balloon 18 so as to position the distal end of the ultra-thin distal section 34 proximal to the proximal end of the balloon 18. This will allow balloon expansion of the stent 40. The system 10 dimensions are such that the stent 40 is completely uncovered when the Tuohy-Borst fitting 36 is pulled back until it is in close proximity to the side arm 21 at the proximal end of the balloon angioplasty catheter 20.

It is envisioned that the ultra-thin distal section 34 of the sheath 30 would have a wall thickness of less than 0.05 mm and may be constructed with wall thickness of 0.025 mm or less.

Current state of the art angioplasty balloons are being constructed with a maximum pre-deployment diameter of less than 0.75 mm. Assuming a wall thickness of 0.12 mm for the stent 40 to obtain good radiopacity and a thickness for the ultra-thin distal section 34 of the sheath 30 of 0.05 mm, the outside diameter of the primary stenting system would be less than 1.1 mm.

The gradually tapered distal tip 15 would typically be 1 to 4 cm long with a taper angle 24 that is typically less than 4 degrees and can be less than 1 degree. The gradually tapered proximal portion 15P of the distal tip 15 should be 25% to 75% of the length of the entire distal tip 15.

The balloon angioplasty catheter 20 is made from standard materials as is well known in the art of balloon angioplasty. The stent 40 is typically constructed from stainless steel. The stent may be coated with a drug for delivery to the wall of the vessel or may contain a radioisotope. The drug and/or radioisotope may be used to prevent the formation of neointimal hyperplasia that results from stent implantation into the wall of a blood vessel. The proximal section 32 of the sheath can be constructed from an elastomer such as nylon or urethane, or an elastomer with fine wires wound or braided into the sheath material.

Heat shrinking and solvent swelling processes are two alternative means for shrinking down the ultra-thin distal section 34 of the sheath 30. If heat shrinking is used, the ultra-thin distal section 34 of the sheath would typically be constructed from a material such as the nylon that is used for angioplasty balloons. Such a material could be heat shrunk down over the stent 40 and proximal section 15P of the distal tip 15. If solvent swelling is used, the ultra-thin distal section 34 of the sheath would typically be constructed from a plastic such as polyurethane, Teflon or polyethylene which can be solvent swelled and then shrunk down as the solvent evaporates onto the stent 40 and proximal section 15P of the distal tip 15. The same types of materials and shrinking processes could be used for the securing tube 16.

To facilitate penetration through a tight stenosis, the gradually tapered distal tip 15, securing tube 16 and ultra-thin distal section 34 of the sheath 30 should be lubricity coated.

The operation of the primary stenting system 10 is best explained with the assistance of FIGS. 2A, 2B, 2C, 2D and 2E.

Figure 2A:
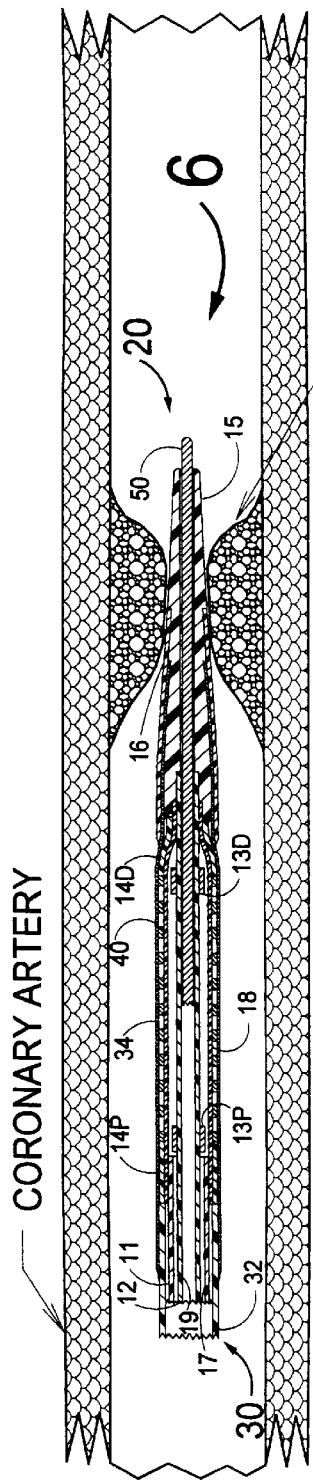
FIG. 2A shows a longitudinal cross section of the distal section of the stent delivery catheter system prior to stent deployment as it is pushed through an arterial stenosis.

FIG. 2A shows the distal section 6 advanced over the guide wire 50 until the tapered tip 15 has begun penetration of an arterial stenosis. It should be understood that the very gradually tapered shape of the tip 15 and the continuous outer surfaces of the tip 15, securing tube 16 and ultra-thin distal sheath section 34 (each of which can have a lubricious outer coating) facilitates entry into an arterial stenosis.

Figure 2B:
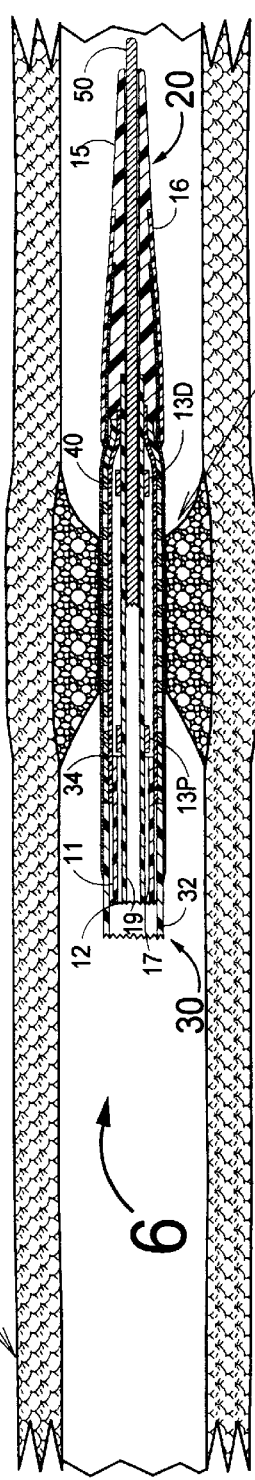
FIG. 2B shows a longitudinal cross section of the distal section of the stent delivery catheter system prior to stent deployment as it would be placed into an arterial stenosis.

FIG. 2B shows the distal section 6 with the non-deployed stent 40 centered within an arterial stenosis. The radiopaque marker bands 13P and 13D are utilized to center the stent 40 with respect to the stenosis.

A most important capability of the primary stenting system 10 is its ability to be pushed through even a very tight stenosis. This capability originates from several specific aspects of the design of the primary stenting system 10, namely, the extraordinarily gradual taper of the lubricity coated distal tip 15, the continuous outer surfaces of the tip 15, securing tube 16 and ultra-thin distal sheath section 34, and the distally directed push force that can be transferred to the distal tip 15 from the distal end 9 of the sheath's proximal section 32. The system 10 obtains its capability to push the distal tip 15 through a tight stenosis by a series of structures each of which is capable of significant pushability. This series of structures that provide excellent pushability for the primary stenting system 10 are:

(1) The Tuohy-Borst fitting 36 at the proximal end of the sheath 30 which fitting lies outside the patient's body.

(2) The comparatively thick-walled, flexible tube forming the sheath proximal section 32 that is typically a composite cylinder made from wire and an elastomer.

(3) The proximal elastic tube 14P that is attached to the proximal end of the angioplasty balloon 18 which transmits the push force from the distal end of the sheath proximal section 32.

(4) The stent 40 which is the next structure that transmits the distally directed push force toward the distal tip 15.

(5) The distal elastomer tube 14D attached to a distal portion of the balloon 18 that next transmits the push force to the distal tip 15 is the last link in the pushability chain that enhances the capability of the primary stenting system 10 to push through a tight stenosis.

In summary, the pushability of the sheath 30 as transferred to a distal portion of the balloon angioplasty catheter 10 can be very much greater than the pushability of the outer shaft 11 and inner shaft 12 by themselves. It should be noted that the design of the primary stenting system 10 allows the distal sheath section 34 to be both very thin-walled and highly flexible and not requiring any contribution to pushability.

The thin-walled, flexible design of the ultra-thin distal sheath section 34 provides improved capability of the system 10 to place the stent 40 in a tight arterial stenosis because its flexibility improves passage through the tortuous vasculature of coronary arteries. In addition, since the ultra-thin distal sheath section 34 need not contribute to system pushability, a wall thickness of 0.05 mm or less can be used. This minimizes the outside diameter (profile) of the system 10 thus again improving the system's capability for placing the stent 40 into a tight stenosis.

Figure 2C:
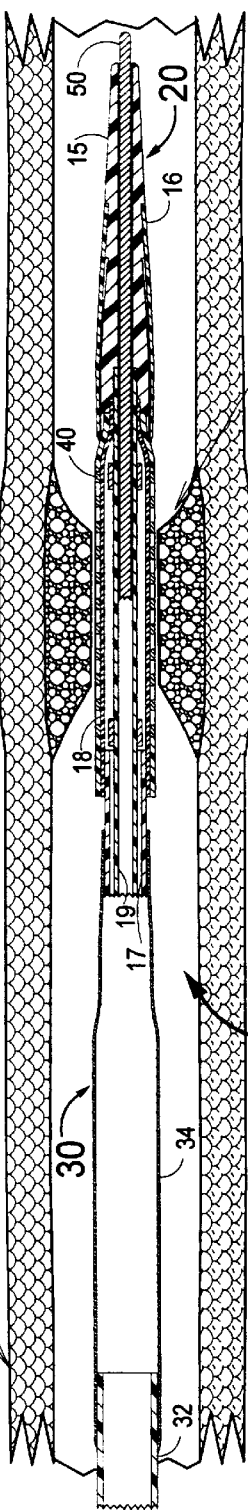
FIG. 2C is a longitudinal cross section of the distal section of the stent delivery catheter system with the sheath pulled back thus uncovering the stent.

FIG. 2C shows the sheath 30 pulled back so the distal end of the ultra-thin distal section 34 is proximal to the proximal end of the balloon 18 and the stent 40 is uncovered and therefore ready to be expanded. Pull back of the sheath 30 is accomplished by holding the Luer fitting 23 at the proximal portion of the stent delivery catheter 10 fixed while pulling back on the nut 35 of the Tuohy-Borst fitting at the distal portion of sheath 30. This is accomplished after the nut 35 is loosened so that the gland 37 slides easily over the outer shaft 11 of the balloon angioplasty catheter 20.

FIG. 2D shows an inflated balloon 18' that causes the deployed stent 40' to dilate the stenosis. It should be noted that the elastomer tubes 14P' and 14D' become distorted when the balloon 18 is inflated. After the balloon 18' is deflated, the tubes 14P' and 14D' revert to their original shape as shown for the tubes 14P and 14D shown in FIGS. 1, 2A, 2B and 2C.

FIG. 2E shows the stent 40' in place with the balloon angioplasty catheter 20, sheath 30 and guide wire 50 removed from the patient's arterial system.

Figure 3:
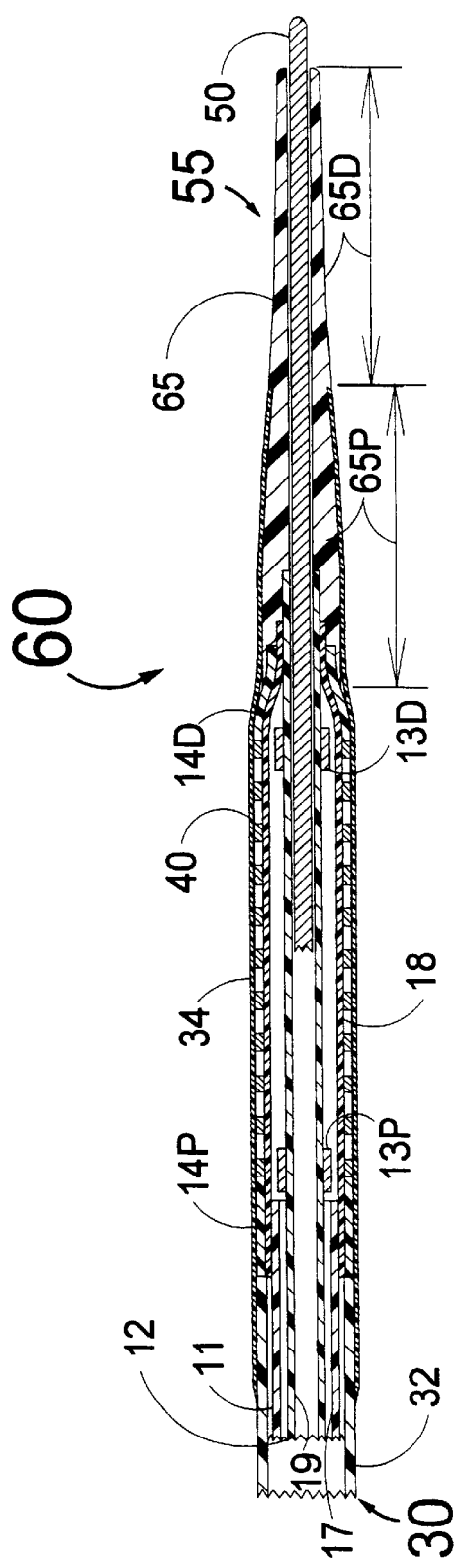
FIG. 3 is a longitudinal cross section of the distal portion of the an alternative embodiment of the sheathed primary stenting system

FIG. 3 is a longitudinal cross section of an alternative embodiment of the present invention. FIG. 3 shows the distal section of a sheathed primary stenting system 60 in its pre-deployment configuration. In this embodiment the sheath 30 is identical to that of the primary stenting system 10 of FIGS. 1 through 2D inclusive. The balloon angioplasty catheter 55 has a gradually tapered distal tip 65 with gradually tapered proximal portion 65P and gradually tapered distal portion 65D. The balloon angioplasty catheter 55 lacks the securing tube 16 which was attached to the gradually tapered distal tip 15 of the balloon angioplasty catheter 20 of FIGS. 1 through 2D inclusive. In the FIG. 3 embodiment, the distal end of the ultra-thin distal section 34 is shrunk down onto the proximal portion 65P of the gradually tapered distal tip 65 and forms a continuous outer surface transition from the gradually tapered distal portion 65D of the tapered tip 64. Otherwise, the proximal end and function of the primary stenting system 60 is identical to the primary stenting system 10 of FIGS. 1 though 2D inclusive. It should be noted that having the ultra-thin distal section 34 of the sheath 30 shrunk down over the entire proximal portion 65P of the tapered tip 65 will help keep the distal end of the ultra-thin distal section 34 secured during advancement through curved vessels.

Figure 4:
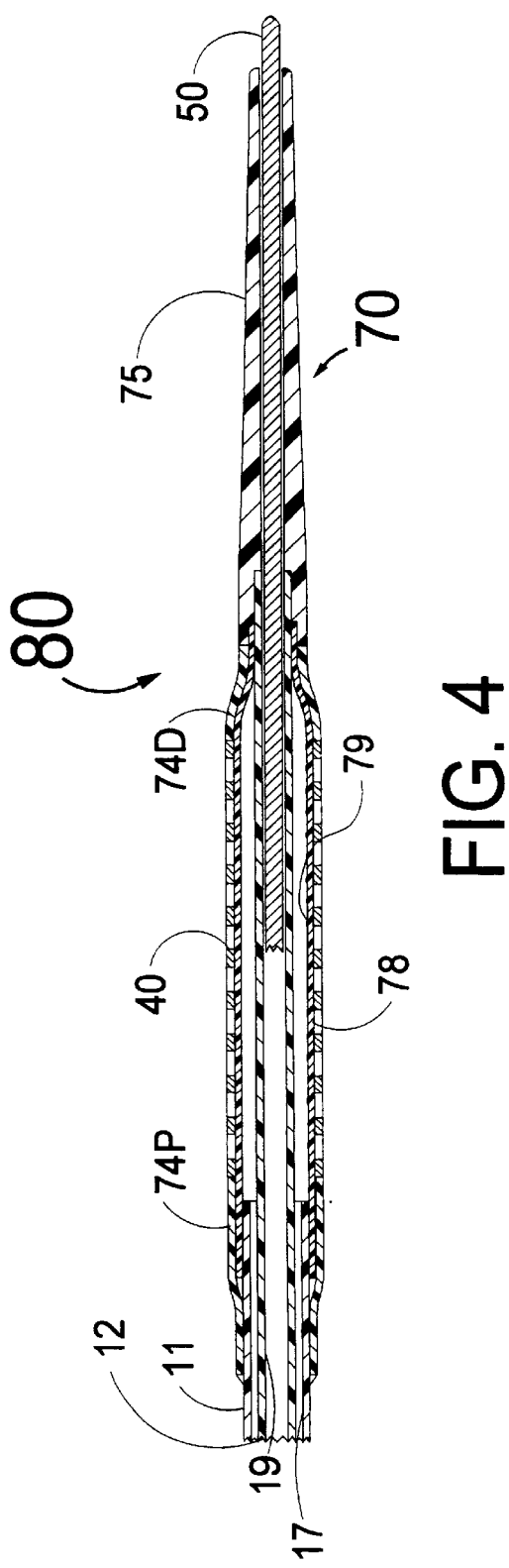
FIG. 4 is a longitudinal cross section of the distal portion of an unsheathed embodiment of the primary stenting system.

FIG. 4 is a longitudinal cross section of another alternative embodiment of the present invention. FIG. 4 shows the distal section of a primary stenting system 80 in its pre-deployment configuration. In this embodiment there is no sheath 30 as in the embodiments of FIGS. 1 and 3. In the FIG. 4 embodiment, the primary stenting system has a stent 40, a balloon angioplasty catheter 70 and a guide wire 50. The proximal end of the balloon angioplasty catheter 70 is identical to the proximal end of the balloon angioplasty catheter 20 of FIG. 1. Furthermore, the balloon angioplasty catheter 70 consists of an outer shaft 11, an inner shaft 12, a proximal radiopaque elastomer band 74P, a distal radiopaque elastomer band 74D and a distal elastomer tapered tip 75. The balloon angioplasty catheter 70 has a central lumen 19 and an annular balloon inflation lumen 17. The balloon angioplasty catheter 70 also has an angioplasty balloon 78 whose interior chamber 79 is in fluid communication with the annular balloon inflation lumen 17. Mounted on the balloon 78 is a balloon expandable stent 40 of any design that is well known in the art of balloon expandable stents. The radiopaque elastomer bands 74P and 74D eliminate the need for separate radiopaque marker bands 13P and 13D of the balloon angioplasty catheter 20 of FIG. 1. Eliminating the internal radiopaque marker bands 13P and 13D allows a lower profile for the system 60. The elastomer bands 74P and 74D are typically made from a highly elastic material such as polyurethane or silicone rubber into which a high density material such as tungsten (typically in powdered form) has been mixed.

It should be understood that radiopaque elastomer bands 74P and 74D of FIG. 4 could be used in the place of elastomer bands 14P and 14D in the previous embodiment 10 shown in FIGS. 1 through 2E inclusive or in the embodiment 60 shown in FIG. 3. If the radiopaque elastomer bands 74P and 74D are used in system 10 or 60 they eliminate the need for separate radiopaque marker bands 13P and 13D and make the system 10 or 60 lower in profile than if the bands 13P and 13D were present FIG. 5A is a longitudinal cross section of the distal portion of another alternative embodiment of the present invention which is a primary stenting system 100A shown in its pre-deployment configuration. The primary stenting system 100A consists of a balloon angioplasty catheter 110, a slideable sheath 120, a stent 140 and a guide wire 50.

The balloon angioplasty catheter 110 consists of an outer shaft 111, an inner shaft 112, a proximal radiopaque marker band 113P, a distal radiopaque marker band 113D, an elastomer band 114 and a sheath securing tube 115. The distal end of the sheath securing tube 115 is fixedly attached to the distal end of the inner shaft 112 of the balloon angioplasty catheter 110. The balloon angioplasty catheter 110 also has a folded angioplasty balloon 118 whose interior chamber 129 is in fluid communication with the annular passageway 117 used for balloon inflation. Although the folds of the balloon 118 are shown in FIG. 5A, the balloon 118 is not substantially different from the balloon 18 of FIG. 1 where the folds are not shown. Both balloons 18 and 118 are typical of angioplasty balloons that are well known in the art of balloon angioplasty. In this embodiment, the distal tip 116 is the distal extension of the inner shaft 112 beyond the distal end of the balloon 118.

Mounted on the balloon 118 is a balloon expandable stent 140 of any design that is well known in the art of balloon expandable stents. The proximal and distal radiopaque markers 113P and 113D are swaged into the inner shaft 112 so as to not protrude against the angioplasty balloon 118 thus providing a minimum profile for the system 100A.

The slideable sheath 120 is situated coaxially about the balloon angioplasty catheter 110. The distal portion of the sheath 120 shown in FIG. 5A comprises an ultra-thin distal section 124 and a sheath proximal section 122. The proximal section 122 of the sheath 120 is identical to the proximal section 32 of the sheath 30 of FIG. 1.

The ultra-thin distal section 124 of the sheath 120 is shrunk down onto the elastomer band 114, the stent 140, the distal end of the balloon 118 and part of the inner shaft 112. The distal end of the securing tube 115 is fixedly attached to the distal end of the distal section 116. The proximal section of the securing tube 115 is tightly shrunk down over the distal portion of the ultra-thin distal section 124 of the sheath 120. This will secure the distal end of the ultra-thin distal section 124 to the inner shaft 112 and create an extremely smooth outer surface for easy sliding around tight curves and for penetration through tight stenoses during delivery of the primary stenting system 100A into the human body. Although the securing tube 115 holds the ultra-thin distal section 124 against the inner shaft 112, the ultra-thin distal section 124 can still be pulled proximally out from under the securing tube 115 so as to uncover the stent 140.

The sheath proximal section 122 has a distal end 9 that is in contact with the proximal end of the elastomer band 114. This causes the push force exerted at the proximal end of the sheath 120 to be transferred from the sheath proximal section 122 through the proximal elastomer band 114 to the distal end of the balloon angioplasty catheter 110. In addition to providing a transfer of push force, the elastomer band 114 will prevent the stent 140 from sliding in a proximal direction during pullback of the sheath 120. The elastomer band 114 is typically made from a highly elastic material such as polyurethane or silicone rubber.

Methods for attaching the distal end of the sheath securing tube 115 to the distal end of the inner shaft 112 include ultrasonic welding and adhesive bonding.

It should be understood that the radiopaque marker bands 13P and 13D of FIGS. 1 through 2D inclusive could be swaged onto the inner shaft 11 like the radiopaque marker bands 113P and 113D of the system 100A of FIG. 5A. Swaged radiopaque marker bands could also be used with the unsheathed primary stenting system 80 of FIG. 4 in which case the elastomer bands 74P and 74D need not contain a radiopacity enhancing material.

The process for assembling the primary stenting system 100A of FIG. 5A, where heat shrinking is used to contract the ultra-thin distal section 124, is as follows:

1. Assemble separately the balloon angioplasty catheter 110 without the elastomer band 114.
2. Assemble the proximal end and proximal section 122 of the sheath 120.
3. Manufacture the stent 140.
4. Insert the distal end of the balloon angioplasty catheter 110 into the proximal end of the sheath 120 and slide the proximal end of the sheath 120 as far as it can go toward the proximal end of the balloon angioplasty catheter 110.
5. Place the elastomer band 114 over the proximal end of the balloon 118.
6. Crimp the stent 140 onto the balloon 118 of the balloon angioplasty catheter 110 just distal to the distal end of the elastomer band 114.
7. Slide the proximal end of the ultra-thin distal section 124 over the distal portion of the balloon angioplasty catheter 110 with stent 140 until the proximal end of the ultra-thin distal section 124 lies just proximal to the distal end of the proximal sheath 122.
8. Fixedly attach by welding or bonding the ultra-thin distal section 124 to the proximal sheath 122.
9. Slide the now joined two part sheath distally until the distal end 9 of the proximal sheath 122 touches the proximal end of the marker band 114.
10. Shrink the ultra-thin distal section 124 down onto elastomer band 114, crimped stent 140, and a portion of the extension of the inner shaft 112 beyond the distal end of the balloon 118.
11. Trim any excess length of ultra-thin distal section 124 until the distal end of the ultra-thin distal section is located at the desired position on the extension of the inner shaft 112 beyond the distal end of the balloon 118.
12. If a securing tube 115 is used, slide it over and shrink it down onto the distal end of the balloon angioplasty catheter 110 and distal end of the shrunk ultra-thin distal section 124.
13. Fixedly attach by welding or bonding, the distal end of the securing tube 115 to the distal end of the distal section 116 of the inner shaft 112.

The system 100A is now ready for final packaging and sterilization.

FIG. 5B is a longitudinal cross section of the distal portion of another embodiment of the sheathed primary stenting system 100B which is a minor variation of the distal portion of the sheathed primary stenting system 100A of FIG. 5A. The only difference between the system 100B of FIG. 5B and the system 100A of FIG. 5A is the securing tube 115 of FIG. 5A which is not present in the system 100B of FIG. 5B.

Figure 6:
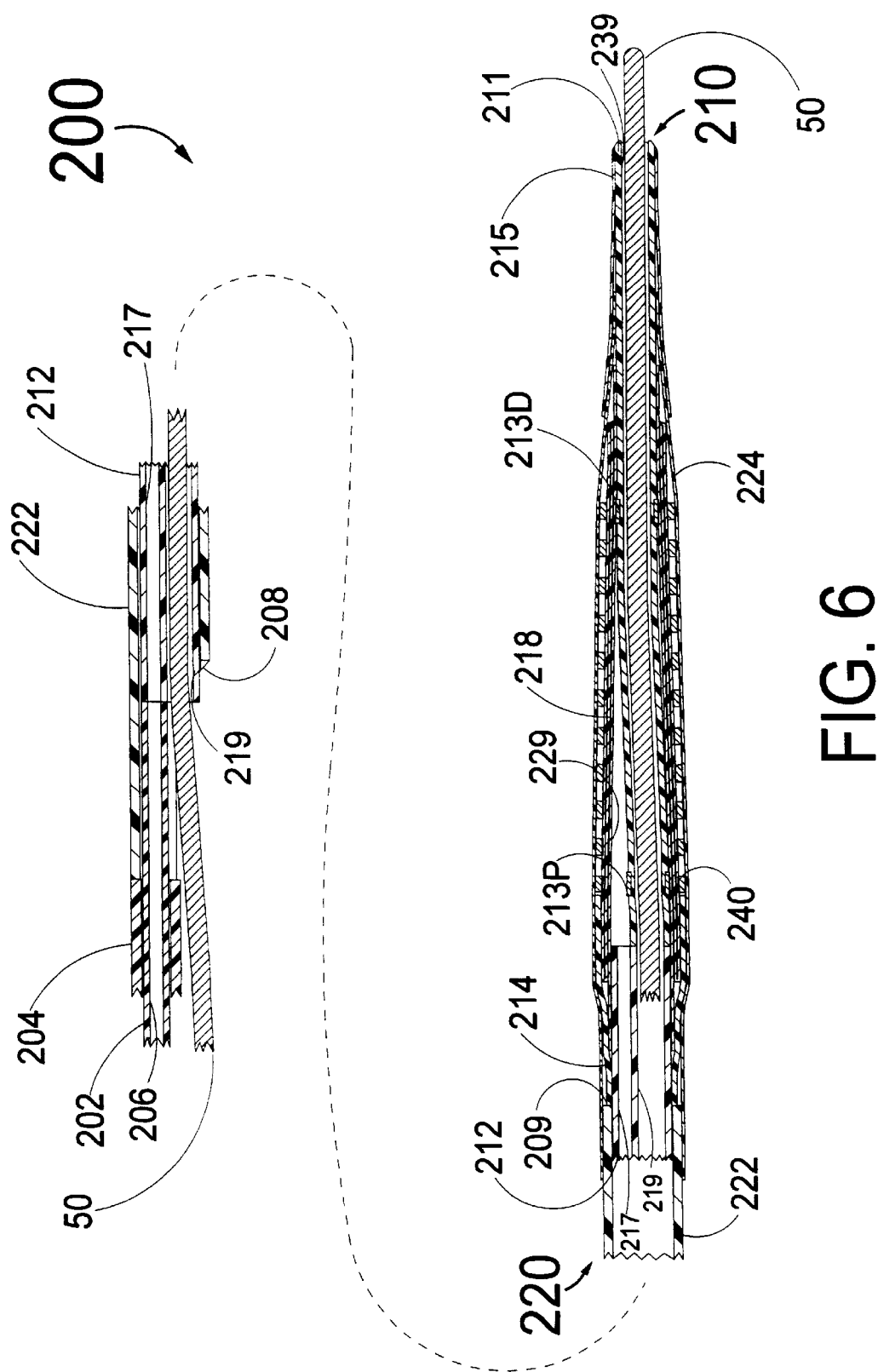
FIG. 6 is a longitudinal cross section of the central and distal portions of a rapid exchange version of the sheathed primary stenting system.

FIG. 6 is a longitudinal cross section of the central and distal portions of a rapid exchange sheathed primary stenting system 200 shown in its pre-deployment configuration.

The rapid exchange primary stenting system 200 consists of a balloon angioplasty catheter 210, a slideable sheath 220, a stent 240 and a guide wire 50.

The balloon angioplasty catheter 210 consists of a proximal shaft 202 with inflation lumen 206 connected to a distal dual lumen shaft 212 with inflation lumen 217 and guide wire lumen 219. The inflation lumen 206 of the proximal shaft 202 is in fluid communication with the inflation lumen 217 of the dual lumen shaft 212. The guide wire lumen 219 has its proximal end at the junction of the proximal shaft 202 and dual lumen shaft 212. The distal end of the dual lumen shaft 212 is connected to a distal guide wire tube 211 so that the guide wire lumen 219 of the dual lumen shaft 212 connects to the lumen 239 of the distal guide wire tube 211.

A proximal radiopaque marker band 213P and a distal radiopaque marker band 213D are swaged onto the distal guide wire tube 211. The balloon angioplasty catheter 210 has a folded angioplasty balloon 218 whose interior chamber 229 is in fluid communication with the lumen 217 used for balloon inflation. The proximal end of the angioplasty balloon 218 is attached to the outside of the dual lumen shaft 212. The distal end of the balloon 218 is attached to the distal guide wire tube 211. Mounted on the balloon 218 is a balloon expandable stent 240 of any design that is well known in the art of balloon expandable stents.

An elastomer band 214 is placed over the proximal end of the balloon 218 and the distal end of the dual lumen shaft 212. A sheath securing tube 215 has its distal end attached to the distal end of the distal guide wire tube 211 of the balloon angioplasty catheter 210.

The slideable sheath 220 is situated coaxially about the balloon angioplasty catheter 210 and has three sections, a proximal section 204, a central section 222 and an ultra-thin distal section 224. The distal end of the proximal section 204 is fixedly attached to the proximal end of the central section 222 of the sheath 220. The distal end of the central section 222 is attached to the proximal end of the ultra-thin distal section 224. An elongated hole 208 in the central section 222 of the sheath 220 allows the guide wire 50 to exit and extend proximally outside of the proximal section 204 thereby creating a rapid exchange or monorail configuration for the sheathed primary stenting system 200. The proximal end of the sheath 220 is similar to that of the sheath 30 of FIG. 2.

The ultra-thin distal section 224 is shrunk down onto the elastomer band 214, the stent 240, the distal end of the balloon 218 and the distal end of the guide wire tube 211. The distal end of a securing tube 215 is fixedly attached to the distal end of the guide wire tube 211. The proximal section of the securing tube 215 is shrunk tight down over the distal portion of the ultra-thin distal section 224 of the sheath 220. This secures the distal end of the ultra-thin distal section 224 to the guide wire tube 211 and creates an extremely smooth outer surface for passage through tortuous coronary vasculature and for penetration through tight stenoses during delivery of the primary stenting system 200. Although the securing tube 215 holds the ultra-thin distal section 224 against the guide wire tube 211, the ultra-thin distal section 224 can still be pulled proximally out from under the securing tube 215 so as to uncover the stent 240.

The sheath central section 222 has a distal end 209 that is in contact with the proximal end of the elastomer band 214. This causes the push force exerted at the proximal end of the sheath 220 to be transferred from the sheath proximal section 204 to the sheath central section 222 through the proximal elastomer band 214 to the distal end of the balloon angioplasty catheter 210. In addition to providing a transfer of push force, the elastomer band 214 prevents the stent 240 from sliding in a proximal direction during pullback of the sheath 220. The elastomer band 214 is typically made from a highly elastic material such as polyurethane or silicone rubber.

The dual lumen shaft 212 of the balloon angioplasty catheter 210 is typically 2 to 20 cm long. This places the exit of the guide wire 50 from the guide wire lumen 219 at the proximal end of the dual lumen shaft 212 approximately 4 to 24 cm from the distal end of the balloon angioplasty catheter 210.

Figure 7:
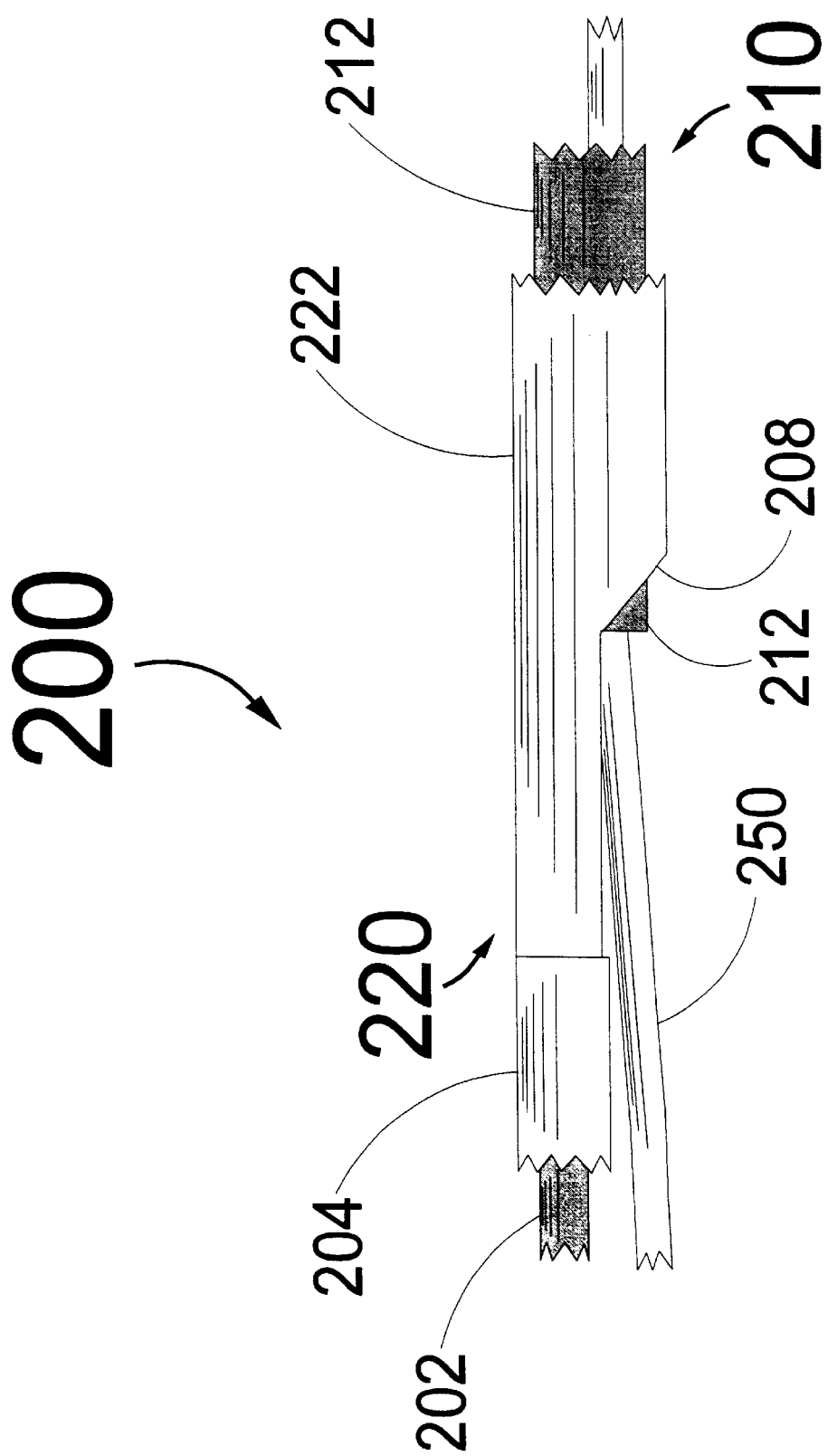
FIG. 7 is a side view of the central portion of the rapid exchange version of the sheathed primary stenting system as shown in FIG. 6.

FIG. 7 is a side view of the central portion of the rapid exchange version of the sheathed primary stenting system 200 of FIG. 6 in its pre-deployment configuration. The portions of the balloon angioplasty catheter 210 shown in FIG. 7 are the proximal shaft 202 and the dual lumen shaft 212. In FIG. 7 the exit of the guide wire 50 from the proximal end of the dual lumen shaft 212 through the hole 208 in the central section 222 of the sheath 220 is clearly seen. The sheath 220 can be pulled back a distance equal to the stent length plus several centimeters to uncover the stent 50. Even when the sheath 220 is pulled back over some of the guide wire 50 that extends outside the sheath 220, the proximal section of the guide wire 50 will continue to exit from the hole 208 of the central section 222 of the sheath 220. This design permits the primary stenting system 200 to operate as a rapid exchange device.

Although the primary stenting systems 10, 60, 80, 100A and 200 as shown in FIGS. 1 through 7 inclusive are most valuable for stenting of stenosis in coronary arteries, it should be understood that these systems can be used in any vessel of the human body. It should also be noted that the primary stenting systems 10, 60, 80, 100A and 200 can each be readily used in tight arterial stenoses without requiring pre-dilatation. This capability for stent insertion without pre-dilatation saves both time and cost when placing stents into an arterial stenosis. It should also be noted that the elastomer bands 14P and 14D of the systems 10 and 60 and the radiopaque elastomer bands 74P and 74D of the system 80 exactly center the stent 40 on the balloons 18 and 78 respectively.

All of the above embodiments provide excellent protection from inadvertent stent loss and embolization during a procedure. This advantage makes the present invention of particular importance when the stents used are radioactive as described by Fischell et al in U.S. Pat. No. 5,059,166.

Various other modifications, adaptations, and alternative designs are of course possible in light of the above teachings. Therefore, it should be understood at this time that within the scope of the appended claims, the invention could be practiced otherwise than as specifically described herein.

What is claimed is:

1. In combination, a primary stenting system for placing a stent within a stenosis of a vessel in a human body, the system comprising:

a flexible guide wire;

a balloon angioplasty catheter having a distal portion, the balloon angioplasty catheter having an inflatable balloon located at its distal portion, the inflatable balloon having a proximal end and a distal end, the balloon angioplasty catheter also having a lumen through which the guide wire can be slideably moved, the balloon angioplasty catheter also having a distal tip which extends distal to the distal end of the balloon toward the distal end of the balloon angioplasty catheter, the distal tip having a proximal end and a distal end, a stent coaxially mounted around the inflatable balloon of the balloon angioplasty catheter the stent having a proximal end and a distal end;

a sheath generally in the form of a cylindrical tube that is coaxially located around the balloon angioplasty catheter with its coaxially mounted stent, the sheath having a proximal section and an ultra-thin distal section, the proximal section of the sheath having a proximal end and a distal end, the ultra-thin distal section of the sheath having a proximal end and a distal end, the proximal end of the ultra-thin distal section of the sheath being fixedly attached to the distal end of the proximal section of the sheath, said sheath ultra-thin distal section being shrunk down onto the distal portion of the balloon angioplasty catheter including its coaxially mounted stent, the sheath being adapted to be slideably retracted in a proximal direction so that the distal end of the ultra-thin section of the sheath lies proximal to the balloon so that the stent can be radially expanded when the balloon is inflated; and system further comprising an elastomer securing tube having a proximal section and a distal section, the distal section being fixedly attached to the distal end of the distal tip and the proximal section of the elastomer securing tube being placed over the distal end of the ultra-thin section of the sheath.

2. The system of claim 1 wherein the wall thickness of said sheath proximal section being more than twice the wall thickness of said sheath ultra-thin distal section.

3. The system of claim 1 wherein the wall thickness of the ultra-thin distal section of the sheath is less than 0.05 mm.

4. The system of claim 1 wherein the wall thickness of the ultra-thin distal section of the sheath is less than 0.025 mm.

5. The system of claim 1 wherein the ultra-thin distal section of the sheath is made from a heat shrinkable polymer.

6. The system of claim 1 wherein the ultra-thin distal section is made of nylon.

7. The system of claim 1 wherein the ultra-thin distal section of the sheath is made from a solvent swellable material.

8. The system of claim 1 wherein the ultra-thin distal section of the sheath is lubricity coated.

9. The system of claim 1 wherein the distal tip is more than 10 mm long.

10. The system of claim 1 wherein the distal tip is more than 20 mm long.

11. The system of claim 1 wherein the distal tip is tapered from a larger diameter at its proximal end to a smaller diameter at its distal end.

12. The system of claim 11 wherein the distal tip has an average taper of less than 4 degrees from its distal end to its proximal end.

13. The system of claim 1 wherein the balloon angioplasty catheter further comprises a coaxially mounted elastomer band placed coaxially over the angioplasty catheter just proximal to the stent, the elastomer band being adapted to prevent the stent from sliding in a proximal direction.

14. The system of claim 13 wherein the elastomer band includes a high density material for increased radiopacity.

15. The system of claim 13 wherein the elastomer band has a proximal end and a distal end and the distal end of the proximal section of the sheath is adapted to provide distally directed push force against the proximal end of the elastomer band.

16. The system of claim 13 wherein the balloon angioplasty catheter further comprises a coaxially mounted distal elastomer band placed coaxially over the angioplasty catheter just distal to the stent, the distal elastomer band being adapted to prevent the stent from sliding in a distal direction.

17. The system of claim 16 wherein the distal elastomer band includes a high density material for increased radiopacity.

18. The system of claim 1 wherein the primary stenting system is an over-the-wire stent delivery catheter system.

19. The system of claim 1 wherein the primary stenting system is a rapid exchange stent delivery catheter system.

20. In combination, a primary stenting system for placing a stent within a stenosis of a vessel in a human body, the system comprising:

a flexible guide wire;

a balloon angioplasty catheter having a distal portion, the balloon angioplasty catheter having an inflatable balloon located at its distal portion, the inflatable balloon having a proximal end and a distal end, the balloon angioplasty catheter also having a lumen through which the guide wire can be slideably moved, the balloon angioplasty catheter also having a distal tip which extends distal to the distal end of the balloon toward the distal end of the balloon angioplasty catheter, the distal tip having a proximal end and a distal end, a stent coaxially mounted around the inflatable balloon of the balloon angioplasty catheter, a sheath generally in the form of a cylindrical tube that is coaxially located around the balloon angioplasty catheter with its coaxially mounted stent, the sheath having an ultra-thin distal section, the ultra-thin distal section of the sheath being shrunk down onto the distal portion of the balloon angioplasty catheter including its coaxially mounted stent, said shaft ultra-thin distal section being situated between the distal end of the angioplasty balloon and the distal end of the distal tip; and an elastomer securing tube having a proximal section and a distal section, the distal section being fixedly attached to the distal end of the distal tip of the balloon angioplasty catheter and the proximal section of the elastomer securing tube being adapted to cover the distal end of the ultra-thin section of the sheath, the sheath being adapted to be slideably retracted in a proximal direction from under the securing tube.

21. The system of claim 20 wherein the wall thickness of the securing tube is less than 0.05 mm.

22. The system of claim 20 wherein the wall thickness of the securing tube is less than 0.025 mm.

23. The system of claim 20 wherein the wall thickness of the ultra-thin distal section of the sheath is less than 0.05 mm.

24. The system of claim 20 wherein the wall thickness of the ultra-thin distal section of the sheath is less than 0.025 mm.

25. The system of claim 20 wherein the ultra-thin distal section of the sheath is made from a heat shrinkable polymer.

26. The system of claim 20 wherein the ultra-thin distal section is made of nylon.

27. The system of claim 20 wherein the securing tube is made of nylon.

28. The system of claim 20 wherein the ultra-thin distal section of the sheath is made from a solvent swellable material.

29. The system of claim 20 wherein the ultra-thin distal section of the sheath is lubricity coated.

30. The system of claim 20 wherein the distal tip is more than 10 mm long.

31. The system of claim 20 wherein the distal tip is more than 20 mm long.

32. The system of claim 20 wherein the primary stenting system is an over the wire device.

33. The system of claim 20 wherein the primary stenting system is a rapid exchange stent delivery catheter system.

34. The system of claim 20 wherein the distal tip is tapered from a larger diameter at its proximal end to a smaller diameter at its distal end.

35. The system of claim 34 wherein the distal tip has an average taper of less than 4 degrees from its distal end to its proximal end.

36. The system of claim 21 wherein the balloon angioplasty catheter further comprises a coaxially mounted elastomer band placed coaxially over the angioplasty catheter just proximal to the stent, the elastomer band being adapted to prevent the stent from sliding in a proximal direction when the sheath is slideably retracted in a proximal direction.

37. The system of claim 36 wherein the elastomer band includes a high density material for increased radiopacity.

38. The system of claim 37 wherein the balloon angioplasty catheter further comprises a coaxially mounted distal elastomer band placed coaxially over the angioplasty catheter just distal to the stent, the distal elastomer band being adapted to prevent the stent from sliding in a distal direction after the sheath has been slideably retracted in a proximal direction.

39. The system of claim 38 wherein the distal elastomer band includes a high density material for increased radiopacity.

* * * * *